(12) United States Patent
Fukunaga et al.

(10) Patent No.: US 10,925,796 B2
(45) Date of Patent: Feb. 23, 2021

(54) WALKING TRAINING APPARATUS AND CONTROL METHOD THEREOF

(71) Applicant: TOYOTA JIDOSHA KABUSHIKI KAISHA, Toyota (JP)

(72) Inventors: Daiki Fukunaga, Toyota (JP); Kanako Suzuki, Toyota (JP); Yu Sasaki, Toyota (JP); Uori Koike, Toyota (JP); Masatomo Tanaka, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/210,032

(22) Filed: Dec. 5, 2018

(65) Prior Publication Data

US 2019/0216669 A1  Jul. 18, 2019

(30) Foreign Application Priority Data

Jan. 18, 2018 (JP) .............................. JP2018-006576

(51) Int. Cl.
*A61H 3/00* (2006.01)
*A63B 21/00* (2006.01)
(Continued)

(52) U.S. Cl.
CPC ............. *A61H 1/0262* (2013.01); *A61H 1/00* (2013.01); *A61H 1/024* (2013.01); *A61H 3/008* (2013.01);
(Continued)

(58) Field of Classification Search
CPC ........ A61H 1/0262; A61H 1/00; A61H 1/024; A61H 3/008; A61H 2201/5069; A61H 2201/5007; A61H 1/0229; A61H 1/0266; A61H 2205/10; A61H 2203/0406; A61H 2201/5092; A61H 2201/5064; A61H 2201/5061; A61H 2201/5046; A61H 2201/5043; A61H 2201/1652; A61H 2201/163; A61H 2201/1642; A61H 2201/14; A61H 2201/1215; A61H 2003/007; A61H 2003/005; A61H 3/00;
(Continued)

(56) References Cited

U.S. PATENT DOCUMENTS 5,020,790 A * 6/1991 Beard .................. A61F 5/0102
 482/4
5,667,461 A * 9/1997 Hall ..................... A61H 1/0229
 472/15

(Continued)

FOREIGN PATENT DOCUMENTS

JP  2017-051464  3/2017

*Primary Examiner* — Nyca T Nguyen
(74) *Attorney, Agent, or Firm* — Oblon, McClelland, Maier & Neustadt, L.L.P.

(57) ABSTRACT

A first exemplary aspect is a walking training apparatus including: an walking assistance apparatus attached to a lower limb of a trainee; at least one wire connected to the lower limb directly or through the walking assistance apparatus; a first wire winding mechanism configured to wind the wire for applying a pull-up force to the wire; a sensor for detecting displacement information according to a displacement of a position connected to the wire in a lateral direction; and a controller configured to control the first wire winding mechanism based on the displacement information.

6 Claims, 15 Drawing Sheets

(51) Int. Cl.
*A63B 23/04* (2006.01)
*A61H 1/00* (2006.01)
*A61H 1/02* (2006.01)
*A63B 23/035* (2006.01)

(52) U.S. Cl.
CPC .. *A63B 21/00181* (2013.01); *A63B 23/03516* (2013.01); *A63B 23/04* (2013.01); *A61H 2201/5007* (2013.01); *A61H 2201/5069* (2013.01); *A63B 2220/833* (2013.01)

(58) Field of Classification Search
CPC ............ A61F 2005/0155; A61F 5/0127; A61F 5/0123; A63B 23/03516; A63B 23/04; A63B 21/00181; A63B 24/0087; A63B 22/02; A63B 2220/833
See application file for complete search history.

(56) References Cited

U.S. PATENT DOCUMENTS

| | | | | |
|---|---|---|---|---|
| 6,666,831 | B1* | 12/2003 | Edgerton | A61H 1/0237 600/587 |
| 6,821,233 | B1* | 11/2004 | Colombo | A61F 5/0102 482/54 |
| 7,887,471 | B2 | 2/2011 | McSorley | A63B 21/0552 482/136 |
| 7,998,040 | B2* | 8/2011 | Kram | A63B 21/4015 482/124 |
| 8,057,410 | B2* | 11/2011 | Angold | A61H 3/00 601/35 |
| 8,147,436 | B2* | 4/2012 | Agrawal | A63B 22/0235 602/16 |
| 8,308,618 | B2* | 11/2012 | Bayerlein | A61H 1/0237 482/54 |
| 8,562,548 | B2* | 10/2013 | Shimada | A61B 6/037 601/23 |
| 8,608,479 | B2* | 12/2013 | Liu | A61H 1/024 434/255 |
| 8,920,347 | B2* | 12/2014 | Bayerlein | A63B 22/0235 601/35 |
| 9,737,453 | B2* | 8/2017 | Shimada | A63B 22/0046 |
| 2002/0026130 | A1* | 2/2002 | West | A61F 5/0102 601/23 |
| 2003/0064869 | A1* | 4/2003 | Reinkensmeyer | A61B 5/1038 482/100 |
| 2004/0087418 | A1* | 5/2004 | Eldridge | A63B 21/157 482/54 |
| 2004/0116839 | A1* | 6/2004 | Sarkodie-Gyan | A61H 3/008 601/35 |
| 2005/0101448 | A1* | 5/2005 | He | A61H 1/0237 482/54 |
| 2012/0004581 | A1* | 1/2012 | Dinon | A61H 1/0237 601/23 |
| 2012/0197168 | A1* | 8/2012 | Agrawal | A61H 3/008 602/19 |
| 2013/0158444 | A1* | 6/2013 | Herr | A61H 1/0255 601/23 |
| 2014/0100491 | A1* | 4/2014 | Hu | A61H 3/008 601/27 |
| 2014/0190289 | A1* | 7/2014 | Zhu | B25J 9/104 74/89.22 |
| 2014/0201905 | A1* | 7/2014 | Glukhovsky | A61G 7/1049 5/81.1 R |
| 2014/0213951 | A1* | 7/2014 | Pietrusisnki | A61H 1/024 602/23 |
| 2015/0226234 | A1* | 8/2015 | Amundson | A61H 1/0262 60/327 |
| 2015/0320632 | A1* | 11/2015 | Vallery | A61H 3/008 482/69 |
| 2015/0342819 | A1* | 12/2015 | Shimada | A61H 3/00 623/27 |
| 2015/0342820 | A1* | 12/2015 | Shimada | A63B 22/0046 482/69 |
| 2016/0051859 | A1* | 2/2016 | Nakashima | A61H 3/008 482/4 |
| 2016/0136477 | A1* | 5/2016 | Bucher | A63B 22/02 482/4 |
| 2017/0027803 | A1* | 2/2017 | Agrawal | A61B 5/6828 |
| 2017/0035642 | A1* | 2/2017 | Sugata | A63B 22/0046 |
| 2017/0049660 | A1* | 2/2017 | Sugata | A61F 2/70 |
| 2017/0065478 | A1* | 3/2017 | Takashima | A61H 1/0262 |
| 2017/0065849 | A1* | 3/2017 | Konishi | A61B 5/6828 |
| 2017/0071813 | A1* | 3/2017 | Sugata | A63B 22/02 |
| 2017/0119613 | A1* | 5/2017 | Roh | B25J 9/0006 |
| 2018/0036196 | A1* | 2/2018 | Behnke | A63B 24/0087 |
| 2018/0085277 | A1* | 3/2018 | Julin | A61F 5/0102 |
| 2018/0085278 | A1* | 3/2018 | Maekita | A63B 22/0235 |
| 2018/0140496 | A1* | 5/2018 | Sankai | A61H 3/00 |
| 2018/0161230 | A1* | 6/2018 | Maekita | A61B 5/112 |
| 2018/0193217 | A1* | 7/2018 | Von Zitzewitz | A61H 3/008 |
| 2018/0229070 | A1* | 8/2018 | McBride | A63B 21/4001 |

* cited by examiner

WALKING TRAINING APPARATUS AND CONTROL METHOD THEREOF

CROSS REFERENCE TO RELATED APPLICATIONS

This application is based upon and claims the benefit of priority from Japanese patent application No. 2018-6576, filed on Jan. 18, 2018, the disclosure of which is incorporated herein in its entirety by reference.

BACKGROUND

The present disclosure relates to a walking training apparatus and a control method thereof.

A walking training apparatus disclosed in Japanese Unexamined Patent Application Publication No. 2017-51464 includes a walking assistance apparatus attached to a leg of a trainee and a training apparatus by which a trainee does walking training. The training apparatus includes a wire connected to the leg of the trainee through the walking assistance apparatus and a winding mechanism for winding the wire.

SUMMARY

In Japanese Unexamined Patent Application Publication No. 2017-51464, a value of a pull-up force may differ from an appropriate one when the leg of the trainee is widely moved in a lateral direction during walking training.

A first exemplary aspect is a walking training apparatus including: an assisting orthosis attached to a lower limb of a trainee; at least one wire connected to the lower limb directly or through the assisting orthosis; a drive mechanism configured to wind the wire for applying a pull-up force to the wire; a sensor for detecting displacement information according to a displacement of a position connected to the wire in a lateral direction; and a controller configured to control the drive mechanism based on the displacement information.

In the above walking training apparatus, a command value corresponding to the pull-up force is set for the controller and the controller may correct the command value based on the displacement information.

In the above walking training apparatus, the displacement information is a displacement angle θ in a wire direction from a longitudinal direction in a top view and the controller may correct the command value by dividing it by cos θ.

In the above walking training apparatus, the displacement value before correction may be changed according to a walking motion.

In the above walking training apparatus, the wire includes: a first wire connected to the lower limb from a diagonally upper direction in front of a trainee; and a second wire connected to the lower limb from a diagonally upper direction behind the trainee, the drive mechanism includes: a first wire winding mechanism configured to wind the first wire for applying a pull-up force to the first wire; and a second wire winding mechanism configured to wind the second wire for applying a pull-up force to the second wire, and the controller may correct a command value for each of the first and second wire winding mechanisms.

In the walking training apparatus, the sensor is provided for detecting a wire length of each of the first and second wires and the controller may calculate the displacement information based on the wire length.

In the above walking training apparatus, the sensor may include at least one of: a camera for photographing the lower limb; a motion sensor for detecting a motion of the lower limb; a force sensor for detecting a reaction force received by the drive mechanism from the wire; and an angle sensor for detecting a joint angle of the assisting orthosis.

Another exemplary aspect is a control method for a walking training apparatus, the walking training apparatus including: an assisting orthosis attached to a lower limb of a trainee; at least one wire connected to the lower limb directly or through the assisting orthosis; a drive mechanism configured to wind the wire for applying a pull-up force to the wire; and a sensor for detecting displacement information according to a displacement of a position connected to a wire in a lateral direction, and the control method including: obtaining the displacement information based on a detection result of the sensor; and correcting the pull-up force based on the displacement information.

According to the present aspects, it is possible to provide a walking training apparatus and its control method capable of applying an appropriate pull-up force.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Specific embodiments to which the present disclosure is applied will be explained hereinafter in detail with reference to the drawings. However, the present disclosure is not limited to the embodiments shown below. Further, for clarifying the explanation, the following descriptions and the drawings are simplified as appropriate.

[First Embodiment]

Figure 1:
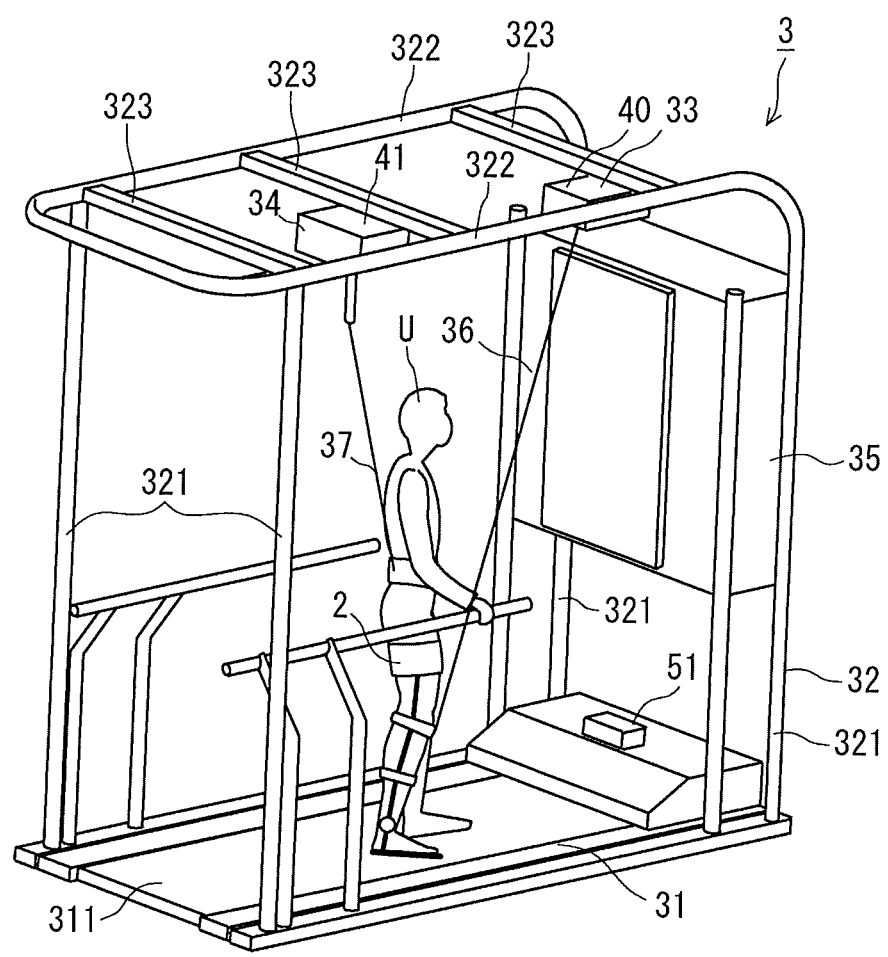
FIG. 1 shows an overall configuration of a walking training apparatus.

FIG. 1 is a perspective view showing a schematic configuration of a walking training apparatus. A walking training apparatus 1 is, for example, an apparatus by which a trainee U such as a patient having hemiplegia caused by a stroke does walking training. The walking training apparatus 1 includes a walking assistance apparatus 2 attached to the leg of the trainee U and a training apparatus 3 by which the trainee U does walking training.

Figure 2:
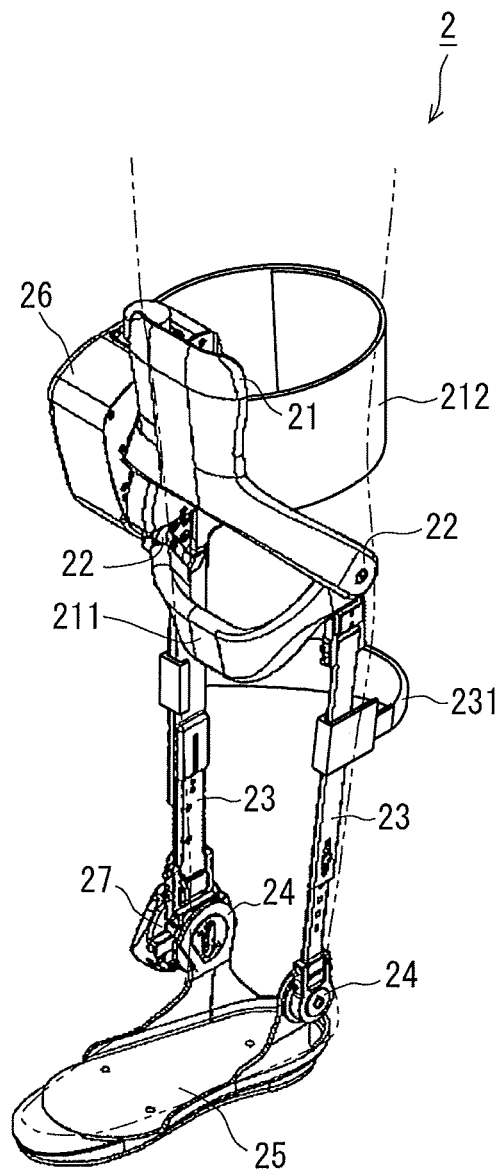
FIG. 2 shows a configuration of a walking assistance apparatus.

The walking assistance apparatus 2 is, for example, attached to a diseased leg of a trainee U who does walking training and assists walking of the trainee U (FIG. 2). The walking assistance apparatus 2 includes an upper leg frame 21, a lower leg frame 23 connected to the upper leg frame 21 through a knee joint part 22, a sole frame 25 connected to the lower leg frame 23 through an ankle joint part 24, a motor unit 26 that rotationally drives the knee joint part 22, and an adjustment mechanism 27 that adjusts the movable range of the ankle joint part 24. Note that the above-described configuration of the walking assistance apparatus 2 is merely an example and the configuration of the walking assistance apparatus 2 is not limited to such an example. For example, the walking assistance apparatus 2 may include another motor unit that rotationally drives the ankle joint part 24.

The upper leg frame 21 is attached to the upper leg of the leg of the trainee U and the lower leg frame 23 is attached to the lower leg of the leg of the trainee U. The upper leg frame 21 is, for example, equipped with an upper leg harness 212 for fixing the upper leg. The upper leg frame 21 is equipped with a horizontally-extending and horizontally-long first frame 211 for connecting with a wire 36 of a first wire winding mechanism 33 (which is described later).

Note that the above-described connecting part of the first wire winding mechanism 33 is merely an example and the connection of the first wire winding mechanism 33 is not limited to such an example. For example, the wire 36 of the first wire winding mechanism 33 may be connected to the upper leg harness 212 and the pulling point of the first wire winding mechanism 33 can be disposed at an arbitrary position in the walking assistance apparatus 2. Note that the wire 36 may directly connect the lower limb of the trainee. A position in which the wire 36 is connected to the walking assistance apparatus 2 or the lower limb is defined as a connecting position. The connecting position may be close to a knee or a foot of the trainee.

The motor unit 26 rotationally drives the knee joint part 22 according to the walking motion of the trainee U and thereby assists the walking of the trainee U. Note that the above-described, configuration of the walking assistance apparatus 2 is merely an example and the configuration of the walking assistance apparatus 2 is not limited to such an example. Any walking assistance apparatus capable of being attached to the lower limb of the trainee U and assisting walking of the trainee U can be applied.

As described above, the walking assistance apparatus 2 is an assisting orthosis attached to the lower limb of the trainee U. Note that the lower limb includes a leg and a foot. The leg includes a thigh (a part of a leg above a knee) and a lower leg (a part of a leg from a knee to an ankle).

The training apparatus 3 includes a treadmill 31, a frame main body 32, first and third wire winding mechanisms 33 and 34, and a control device 35. The treadmill 31 rotates a ring-shaped belt 311. The trainee U gets on the belt 311 and walks on the belt 311 according to the movement of the belt 311. By doing so, the trainee U does the walking training.

The frame main body 32 includes two pairs of pillar frames 321 vertically disposed on the treadmill 31, a pair of lengthwise frames 322 extending in the lengthwise direction and connected to respective pillar frames 321, and three crosswise frames 323 extending in the crosswise direction and connected to each of the lengthwise frames 322. Note that the configuration of the above-described frame main body 32 is merely an example and is not limited to this example.

In the front crosswise frame 323, the first wire winding mechanism 33 that winds the wire 36 connected to the leg of the trainee U directly or through the walking assistance apparatus 2 and thereby pulls the wire 36 is provided. One end of the wire 36, which is pulled by the first wire winding mechanism 33, is connected to the walking assistance apparatus 2. The first wire winding mechanism 33 pulls the walking assistance apparatus 2 upward and forward through the wire 36 by winding the wire 36.

The first wire winding mechanism 33 includes, for example, a mechanism for winding the wire 36 around a rotor and pulling the wire 36 from the rotor, a motor that drives this mechanism, and so on. The first wire winding mechanism 33 is configured so as to wind the wire 36 around the rotor and thereby store the wire 36 in a leg-idling period in the walking motion performed by the trainee U in which the leg of the trainee is in a leg-idling state and pull out the wire 36 from the rotor in a leg-standing period in the walking motion performed by the trainee in which the leg of the trainee U is in a leg-standing state.

Figure 3:
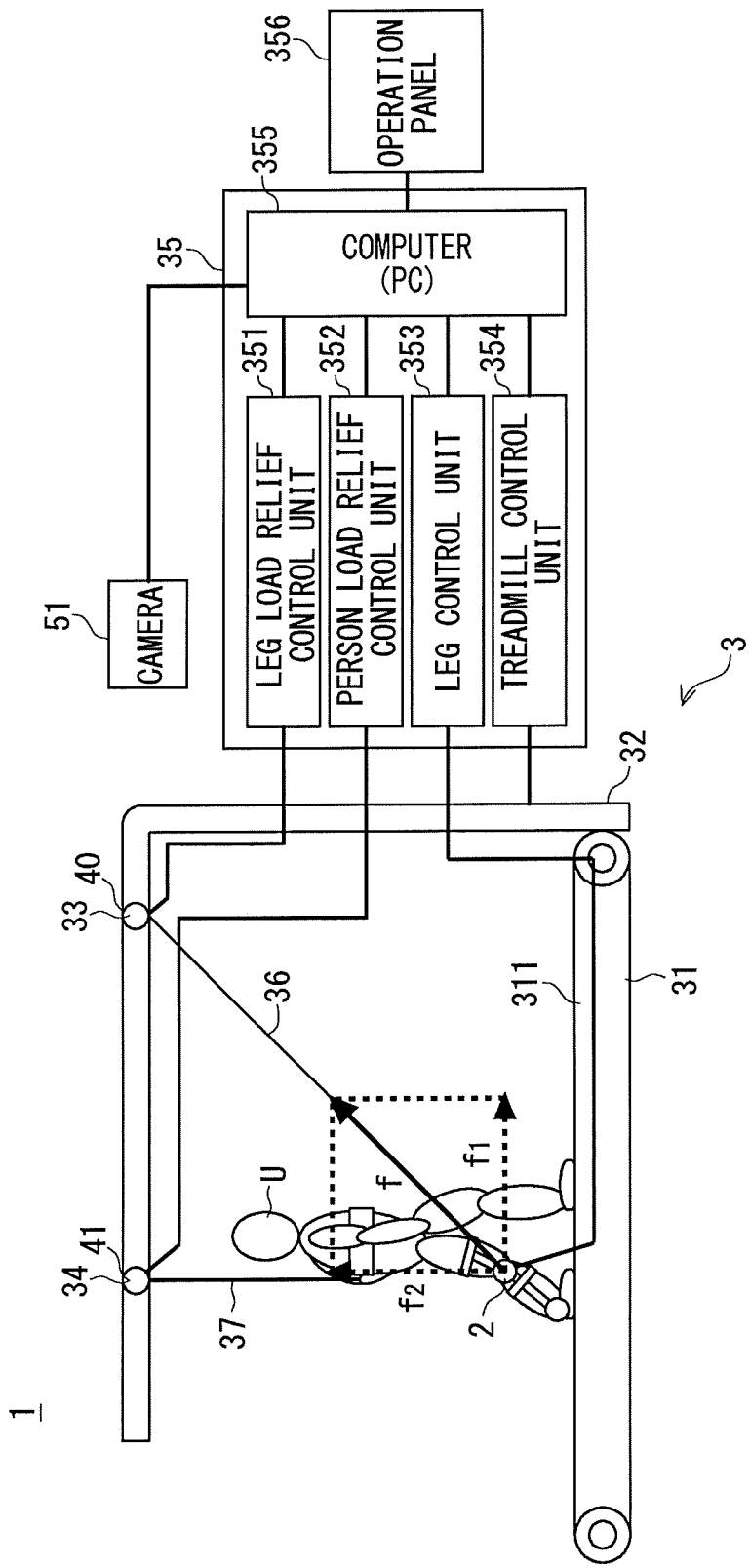
FIG. 3 is a block diagram showing a system configuration of a control device.

The vertically-upward component f2 of the pulling force f applied by the first wire winding mechanism 33 supports the weight of the walking assistance apparatus 2 (FIG. 3). The horizontally-forward component f1 of the pulling force f applied by the first wire winding mechanism 33 assists the start of swinging of the leg. In this way, the walking load of the trainee U in the walking training can be reduced.

The third wire winding mechanism 34 is disposed in the center crosswise frame 323 in a longitudinal direction and pulls a wire 37 upward. One end of the wire 37 is connected to, for example, a belt attached to at or near the waist of the trainee U. The third wire winding mechanism 34 includes, for example, a mechanism for winding the wire 37 around a rotor and pulling the wire 37 from the rotor, a motor that drives this mechanism, and so on. The third wire winding mechanism 34 pulls the waist of the trainee U upward through the wire 37. In this way, the load on the trainee caused by the weight of the trainee U himself/herself can be reduced. Each of the first and third wire winding mechanism 33 and 34 is connected to the control device 35 through a wiring line or the like.

The first and third wire winding mechanisms 33 and 34 include first and third storage amount detection units 40 and 41, respectively, that detect the storage amounts (winding amounts) of the wires 36 and 37, which are wound around the respective rotors of the first and third wire winding mechanisms 33 and 34 and thereby stored therein. A first storage amount detection unit 40 is a specific example of a storage amount detection means (a sensor). The first and third storage amount detection units 40 and 41 detect, for example, the rotation angles and/or the rotation amounts of the rotors by using angle sensors and thereby detect the storage amounts of the wires 36 and 37 wound around the rotors and stored in the wire winding mechanisms. The first and third storage amount detection units 40 and 41 output the detected storage amounts of the wires 36 and 37 to the control device 35. The control device 35 can calculate the wire length from the storage amounts of the wires 36 and 37. Note that the walking training apparatus may include only the first wire winding mechanism 33.

The control device 35 is a specific example of a pulling control means (a controller). The control device 35 controls each of the pulling forces applied by the first and third wire winding mechanisms 33 and 34, the driving of the treadmill 31, and the walking assistance apparatus 2. For example, the control device 35 is formed by hardware mainly using a microcomputer including a CPU (Central Processing Unit) that performs arithmetic processing, control processing, and so on, a memory including a ROM (Read Only Memory) that stores an arithmetic program, a control program and so on to be executed by the CPU, a RAM (Random Access Memory) and so on, and an interface unit (I/F) that externally receives and outputs signals. The CPU, the memory, and the interface unit are connected with each other through a data bus or the like.

The control device 35 controls the first wire winding mechanism 33 so that the first wire winding mechanism 33 pulls the wire 36 with a first pulling force for reducing the weight of the walking assistance apparatus 2 during walking training. The control device 35 controls the first wire winding mechanism 33 so that, for example, the vertically-upward component of the first pulling force applied by the first wire winding mechanism 33 becomes equal to the gravitational force of the walking assistance apparatus 2 during the walking training. As a result, the load on the walking of the trainee U exerted by the gravitational force of the walking assistance apparatus 2 can be reduced. Note that the pulling force of the wire 36 applied by the first wire winding mechanism 33 may be constant or be changed with time.

Further, the walking training apparatus 1 includes a camera 51. For example, the camera 51 is attached to the training apparatus 3. In FIG. 1, the camera 51 is installed in front of the trainee U. However, there are no particular limitations on a position for installing the camera 51. Further, two or more cameras 51 may be installed. The camera 51 photographs a lower limb of the trainee U and the surroundings thereof. It is particularly preferred that the camera 51 photograph a connecting position of the wire 36 with respect to the lower limb (the walking assistance apparatus 2). Then, the camera 51 outputs the photographed image to the control device 35. The control device 35 corrects a pull-up force (a pulling force) based on the photographed image.

FIG. 3 is a block diagram showing a schematic system configuration of the control device according to the first embodiment.

The control device 35 includes, for example, a leg load relief control unit 351 that controls the first wire winding mechanism 33, a person load relief control unit 352 that controls the third wire winding mechanism 34, a leg control unit 353 that controls the walking assistance apparatus 2, a treadmill control unit 354 that controls the treadmill 31, a computer or a PC (Personal Computer) 355 that controls these units, and an operation panel 356 for operating the computer 355. The operation panel 356 displays information such as a training instruction, a training menu, and training information (such as walking speed and biological information). The operation panel 356 is formed, for example, as a touch panel, and a user can enter various types of information through the operation panel 356.

Further, the image from the camera 51 is input to the computer 355. Then, the computer 355 corrects the pull-up force based on the input image. Note that in FIGS. 1 and 3, the first wire winding mechanism 33 pulls up the diseased leg of the trainee U from the diagonally upper direction in front of the trainee U. However, it may pull up the same from the diagonally upper direction behind the trainee U.

Figure 4:
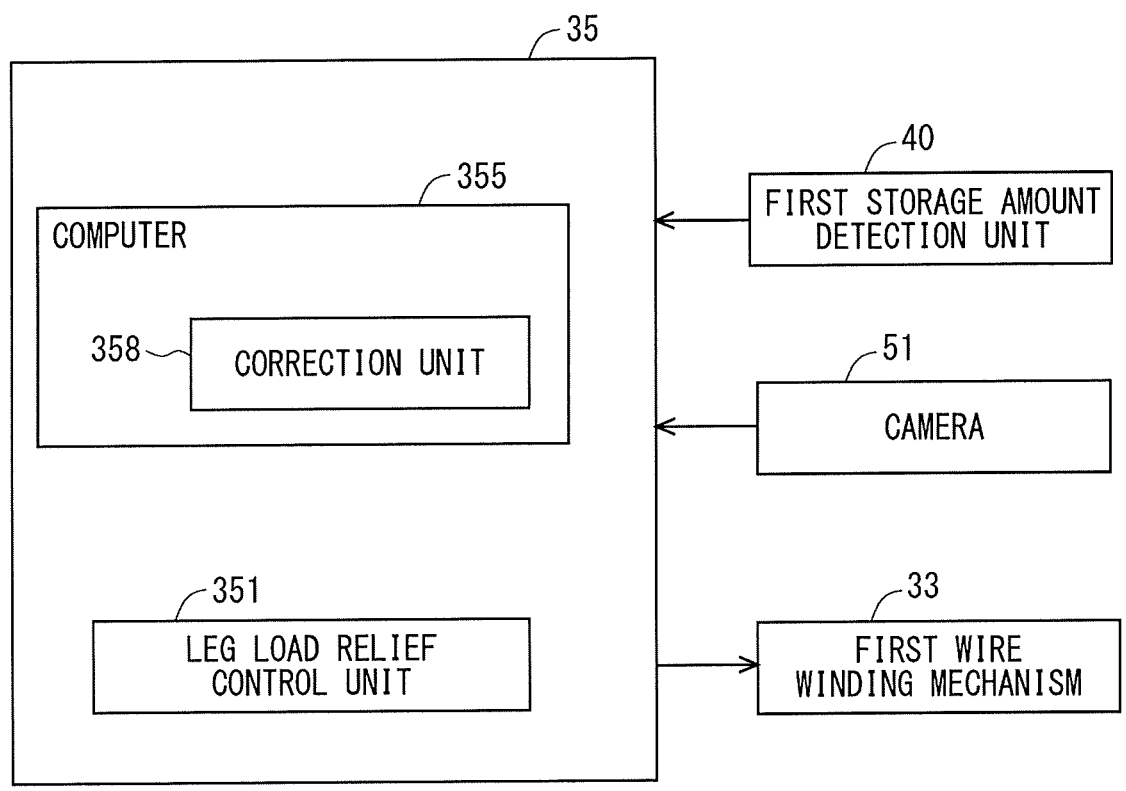
FIG. 4 is a block diagram showing a control system for correcting a pull-up force.

A control system for controlling a pull-up force of the leg load relief control unit 351 is described with reference to FIG. 4. FIG. 4 is a block diagram showing a configuration of the control system.

As shown in FIG. 4, the first storage amount detection unit 40 outputs the storage amount of the wire 36 to the computer 355. The first storage amount detection unit 40 detects the rotation amounts of the motor and the rotor. The first storage amount detection unit 40 includes a rotary encoder or the like. For example, the encoder detects the rotation amount of the motor or the roller. For example, the rotation amount can be detected by integrating a detection value of the encoder. The control device 35 can thereby obtain the storage amount of the wire 36. Further, with the above obtainment of the storage amount of the wire 36, a wire length from the first wire winding mechanism 33 to the connecting position can be obtained.

The camera 51 photographs the lower limb to which the walking assistance apparatus 2 is attached. Then, the camera 51 outputs the photographed image to the computer 355. Note that the camera 51 may photograph only a part of the lower limb instead of the entire lower limb.

The computer 355 includes a correction unit 358 for correcting a pull-up force. The correction unit 358 corrects the pull-up force based on the image from the camera 51. A command value is set for the control device 35 according to the pull-up force. The command value may be a value capable of generating a pull-up force corresponding to the weight of the walking assistance apparatus 2. For example, the control device 35 stores a predetermined command value in the memory. The command value may correspond to motor torque and the like. The correction unit 358 corrects the command value and outputs the corrected command value to the leg load relief control unit 351. That is, the correction unit 358 outputs the command value after the correction to the leg load relief control unit 351.

The leg load relief control unit 351 controls the first wire winding mechanism 33 according to the corrected command value. Further, the wire length has been obtained from the storage amount of the first storage amount detection unit 40. The first wire winding mechanism 33 drives the motor based on the corrected command value to wind the wire 36. The walking assistance apparatus 2 can be thereby pulled up with the corrected pull-up force for the wire 36. Thus, the trainee U can do the walking training while appropriately relieving the load.

Figure 5:
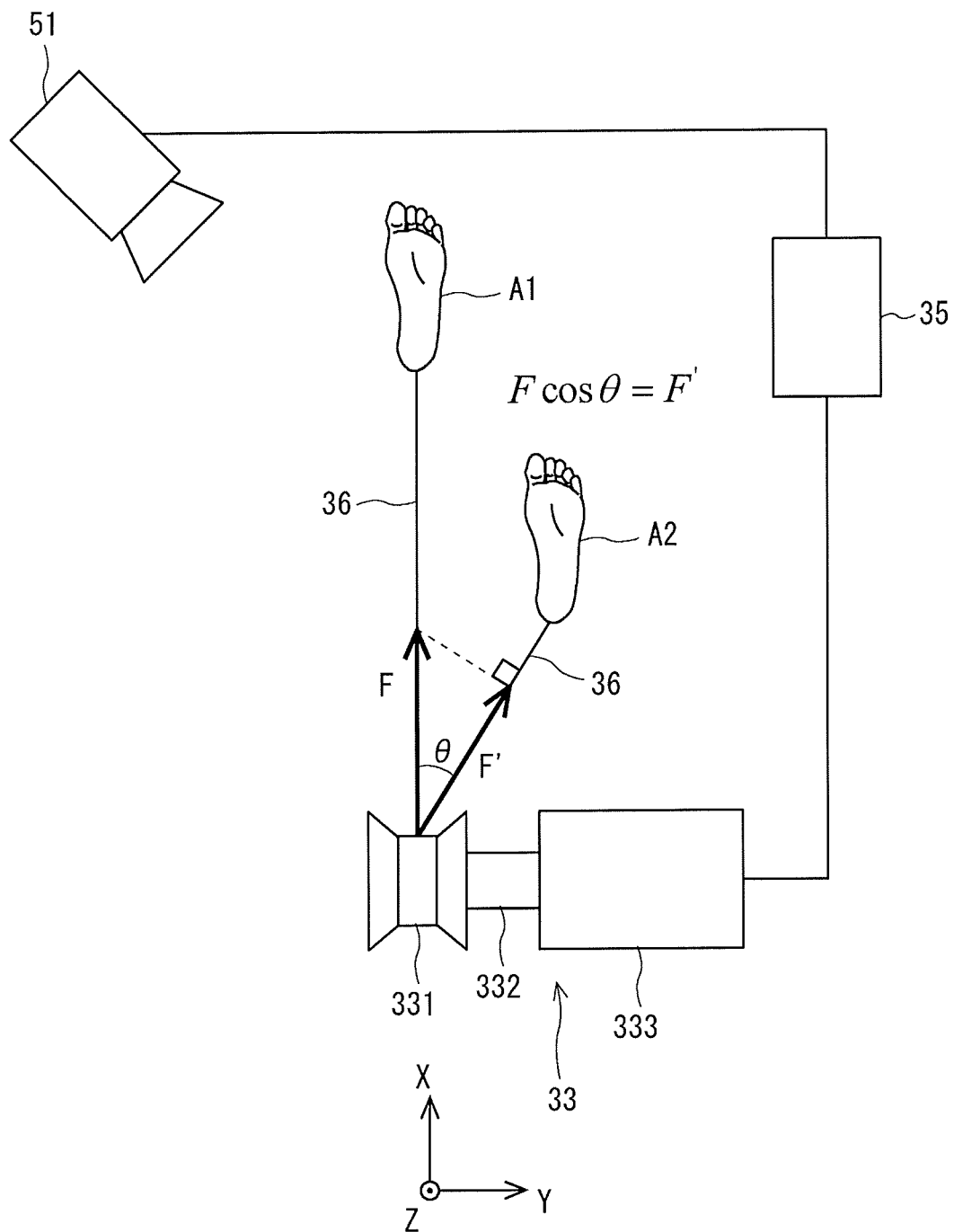
FIG. 5 is a schematic diagram for explaining control for correcting the pull-up force.

The control for correcting the pull-up force is described hereinafter with reference to FIG. 5. FIG. 5 is a schematic diagram for explaining a process for correcting the pull-up force and shows the simplified configuration thereof. FIG. 5 shows a three-dimensional orthogonal coordinate system in which a front direction of the walking direction is defined as a +X direction, a rear direction of the same is defined as a −X direction, a right direction of the same is defined as a +Y direction, a left direction of the same is defined as a −Y direction, a vertically upward direction of the same is defined as a +Z direction, and a vertically downward direction of the same is defined as a −Z direction. Note that the X direction, Y direction, and Z direction are also referred to as a longitudinal direction, a lateral direction (horizontal direction), and a vertical direction, respectively.

An example in which a pull-up force is continuously set to be constant will now be described. That is, it is assumed that a command value F of the pull-up force which is previously set for the control device 35 is constant. Further, FIG. 5 shows a foot position of the diseased leg schematically.

The first wire winding mechanism 33 includes a roller 331, a power transmission shaft 332, and a motor 333. The roller 331 is connected to the motor 333 through the power transmission shaft 332. The wire 36 is wound around the roller 331. The motor 333 rotates according to the command value from the control device 35. The power transmission shaft 332 transfers a rotation force of the motor 333 to the roller 331. The roller 331 can thereby rotate to wind or pull the wire 36. Accordingly, the walking assistance apparatus 2 can be pulled up with the pull-up force according to the command value.

When a foot of the trainee U is in a Y position (Y coordinate) the same as the position of the roller 331, the position of the foot of the trainee U is defined as a foot position A1. Further, when the foot of the trainee U is in the Y position different from the position of the roller 331, the position of the foot of the trainee U is defined as a foot position A2. Note that for simplifying the explanation, it is assumed that a connecting position of the wire 36 with respect to the walking assistance apparatus 2 coincides with the foot position, and the wire 36 is straightly extended between the foot position and the winding position of the roller 331.

In an XY plane view (top view), in the case of the foot position A1, the wire 36 is parallel to the X direction. Therefore, a pull-up force at the foot position A1 coincides with the command value F. On the other hand, in the case of the foot position A2, the foot position A2 in the Y direction is displaced from the roller 331. In the XY plane view, the wire 36 is inclined from the X direction. In the XY plane view, an angle formed between the direction of the wire 36 and the X direction is defined as a displacement angle θ.

When a pull-up force at the foot position A2 is defined as F', F'=F cos θ holds as shown in FIG. 5. When the control device 35 outputs the same command value F to the motor 333, a pull-up force which applies to the wire 36 at each of the foot positions A1 and A2 is different according to the displacement angle θ. That is, the value of the pull-up force F' at the foot position A2 is smaller than the value of the pull-up force F at the foot position A1 by cos θ. In other words, with the increase of θ, the value of the pull-up force F' at the foot position A2 decreases from the command value F. Note that the displacement angle θ is a displacement angle from the X direction in the direction of the wire 36 and the range thereof is between 0° to 90°.

Therefore, in this embodiment, the correction unit 358 corrects the pull-up force according to the displacement amount between the winding position of the first wire winding mechanism 33 and the connecting position of the wire 36. The correction unit 358 specifically calculates a relative position between the connecting position and the roller 331 from the image of the lower limb photographed by the camera 51. The correction unit 358 obtains the displacement angle θ from the relative position between the connecting position and the roller 331 as the displacement information. The correction unit 358 corrects the command value by dividing the predetermined command value F by cos θ.

For example, the correction unit 358 can measure the connecting position of the wire 36 by image-processing the image photographed by the camera 51. The correction unit 358 calculates a connecting position on the XY plane, that is, the X and Y coordinates of the connecting position based on the image photographed by the camera 51. Since the roller 331 is fixed to the crosswise frames 323, the coordinate of the winding position of the roller 331 is known. The wire 36 is stretched between the connecting position with respect to the walking assistance apparatus 2 and the winding position of the roller 331. Therefore, the correction unit 358 can calculate the displacement angle θ. In this case, a stereo camera that photographs the lower limb of the diseased leg from a plurality of directions is preferably used as the camera 51. Obviously, the correction unit 358 image-processes the image from a plurality of directions by installing a plurality of cameras so that the connecting position can be obtained.

Figure 6:
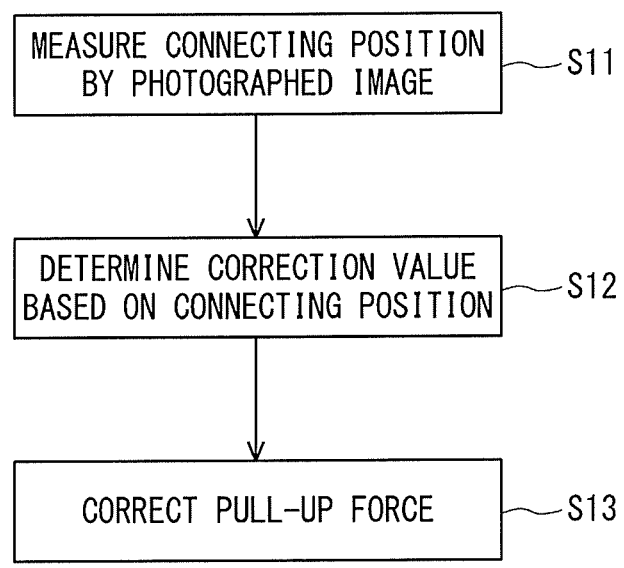
FIG. 6 is a flowchart showing a control method for the walking training apparatus.

Next, a control method for the waking training apparatus 1 is described with respect to FIG. 6. FIG. 6 is a flowchart showing the control method.

First, the correction unit 358 measures a connecting position using the image photographed by the camera 51 (S11). The camera 51 photographs the foot and outputs the photographed image to the control device 35. The correction unit 358 calculates the connecting position of the wire 36 based on the image. Alternatively, the camera 51 may include a processing function of calculating the connecting position from the image. In this case, the connecting position calculated by the camera 51 may be output to the control device 35. That is, the displacement information according to the displacement of the foot position may be calculated by the correction unit 358 or may be detected by the camera 51.

Next, the correction unit 358 determines a correction value based on the connecting position (S12). For example, as described above, the correction unit 358 obtains the displacement angle θ according to the displacement amount of the connecting position as the displacement information. Then, the correction unit 358 corrects the pull-up force (S13). The correction unit 358 outputs the command value according to the corrected pull-up force to the leg load relief control unit 351. For example, the correction unit 358 corrects the command value by dividing the predetermined command value by cos θ. The correction unit 358 outputs the corrected command value to the leg load relief control unit 351. As a result, the first wire winding mechanism 33 can pull up the walking assistance apparatus 2 with the corrected pull-up force.

By performing the above process during the walking training, the walking assistance apparatus 2 can be pulled up with the appropriate pull-up force. Further, the camera 51 has continuously photographed the foot. The correction unit 358 sequentially updates the connecting position based on the foot images which are continuously obtained. In this manner, the pull-up force can be corrected according to the latest connecting position. Since the pull-up force changes according to a walking motion, walking training can be performed with an appropriate pull-up force. Therefore, the walking training can be performed while applying the pull-up force (load relieving force) according to the walking motion of the trainee U.

(Sensor Example 1)

Figure 7:
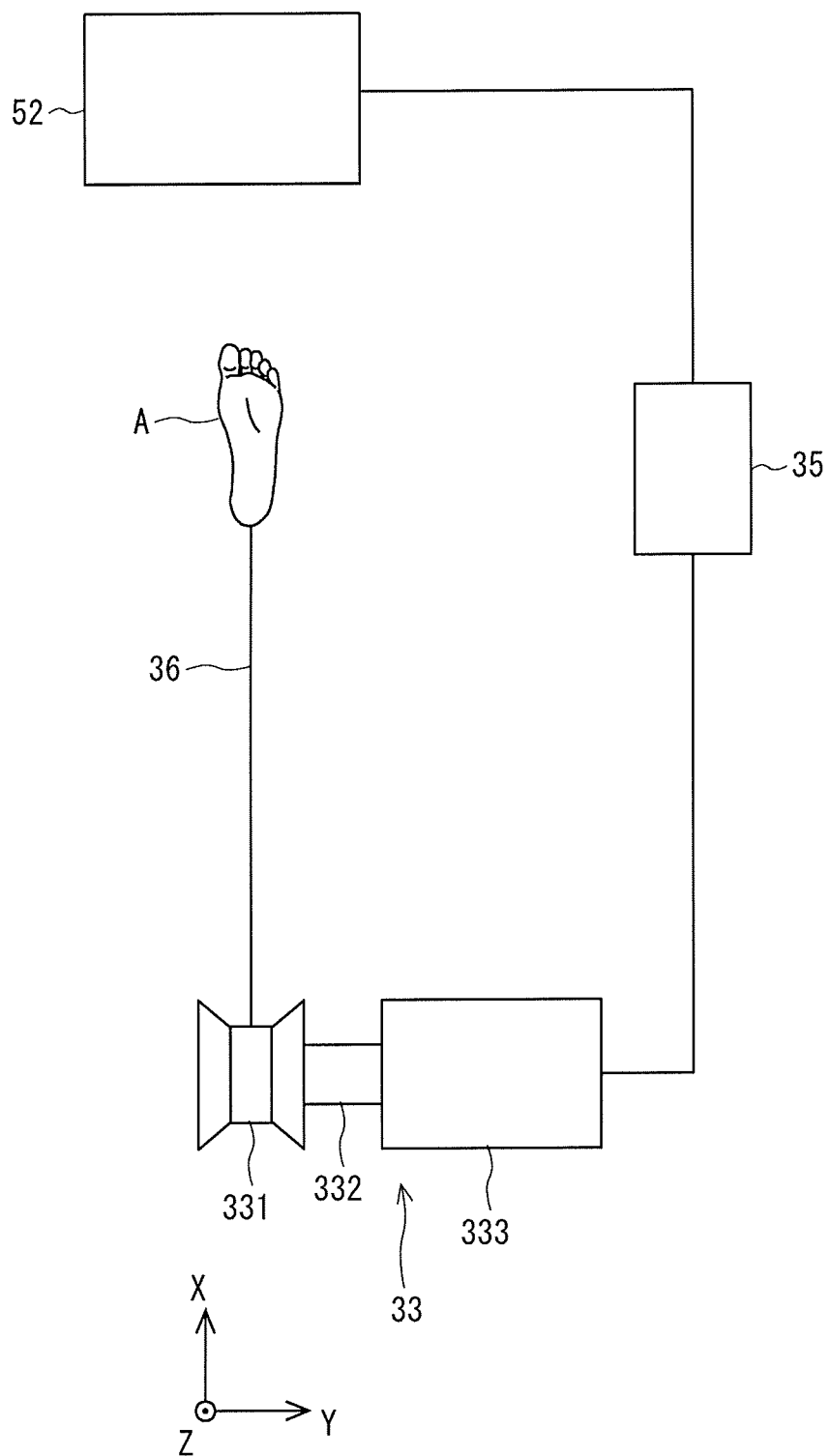
FIG. 7 shows an example 1 of a sensor for measuring a foot position.

Note that the connecting position is measured using the camera 51. However, a sensor unit for measuring the connecting position is not limited to the camera 51. For example, as shown in FIG. 7, a motion sensor 52 may measure the connecting position. The motion sensor 52 measures a motion of the lower limb of the trainee U in the walking motion using motion capture. Sensors such as optical, mechanical and magnetic sensors can be used as the motion sensor 52. For example, a Kinect sensor or the like can be used as the motion sensor 52. Further, a marker may be attached to the foot of the trainee U or the walking assistance apparatus 2. In this case, the motion sensor 52 detects the motion of the lower limb by detecting the attached marker. Then, the motion sensor 52 or the control device 35 detects the connecting position based on the motion of the lower limb. The control device 35 calculates the displacement angle θ based on the detected connecting position. The control device 35 performs the above correction process according to the displacement angle θ.

(Sensor Example 2)

Figure 8:
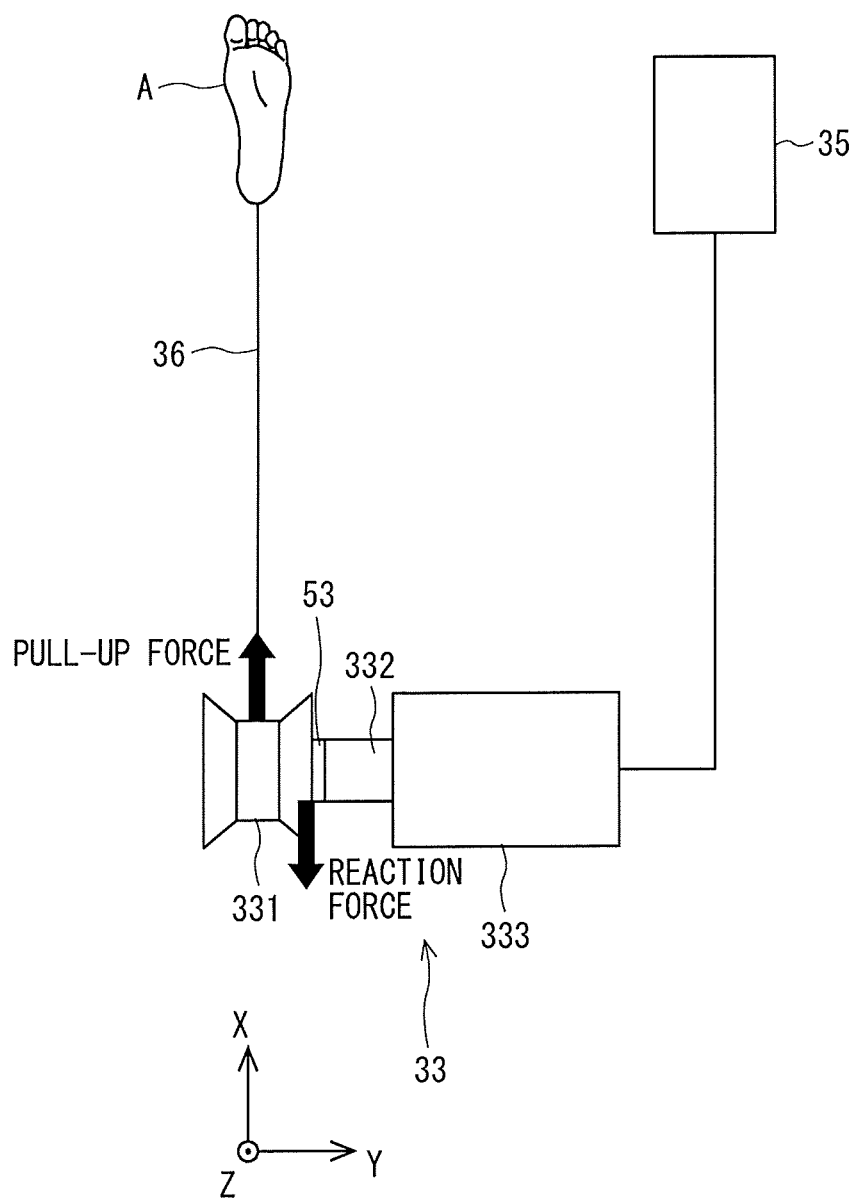
FIG. 8 shows an example 2 of a sensor for measuring the foot position.

Alternatively, as shown in FIG. 8, the displacement angle θ of a foot A may be measured based on a measurement result of a force sensor 53. The force sensor 53 detects a reaction force received by the roller 331 from the wire 36. Then, the control device 35 calculates the displacement angle θ based on a reaction force vector measured by the force sensor 53. As described above, the correction unit 358 corrects the pull-up force according to the displacement angle θ.

(Example of Other Sensors)

Alternatively, an angle sensor provided in each joint of the walking assistance apparatus 2 may obtain the connecting position of the wire 36. For example, the control device 35 calculates the connecting position from angles of each joint detected by the angle sensor.

There are no particular limitations on sensors for measuring the connecting position. Further, two or more sensors may be combined to measure the connecting position. The sensor may directly measure the displacement angle θ instead of calculating the displacement angle θ from the connecting position in the Y direction. The walking training apparatus 1 may include a sensor for detecting the displacement information according to the displacement amount in the lateral direction (Y direction) of the connecting position. Then, the control device 35 corrects the pull-up force based on the displacement information. As a result, the first wire winding mechanism 33 can pull up the foot with an appropriate pull-up force. Further, an appropriate pull-up force can be obtained by using the displacement angle θ as the displacement information.

EXAMPLE 1

Figure 9:
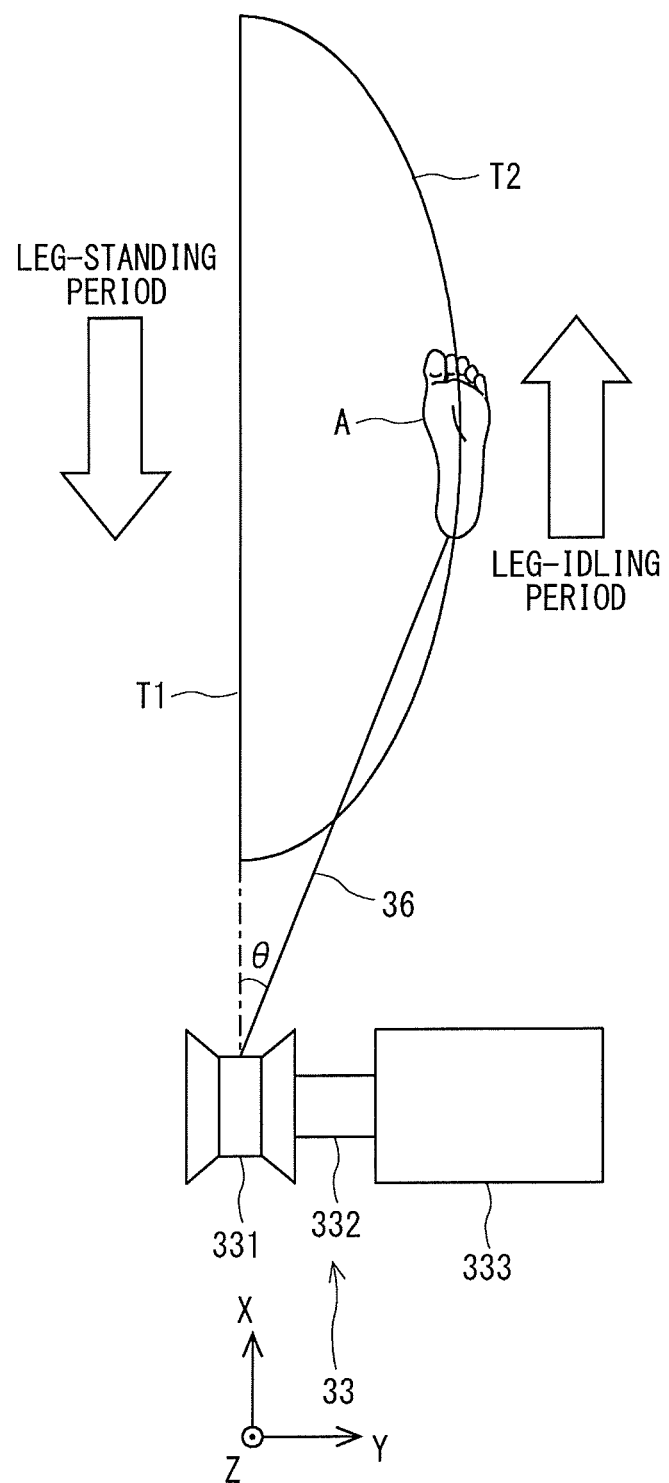
FIG. 9 is a drawing for explaining a change of the foot position in a walking motion.
Figure 10:
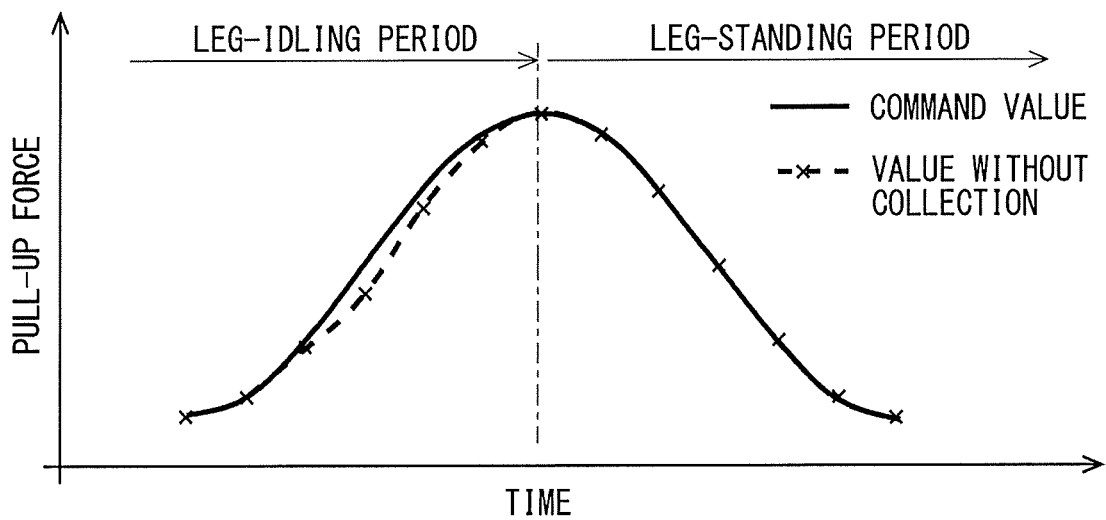
FIG. 10 is a graph showing a time change of a pull-up force without correction.
Figure 11:
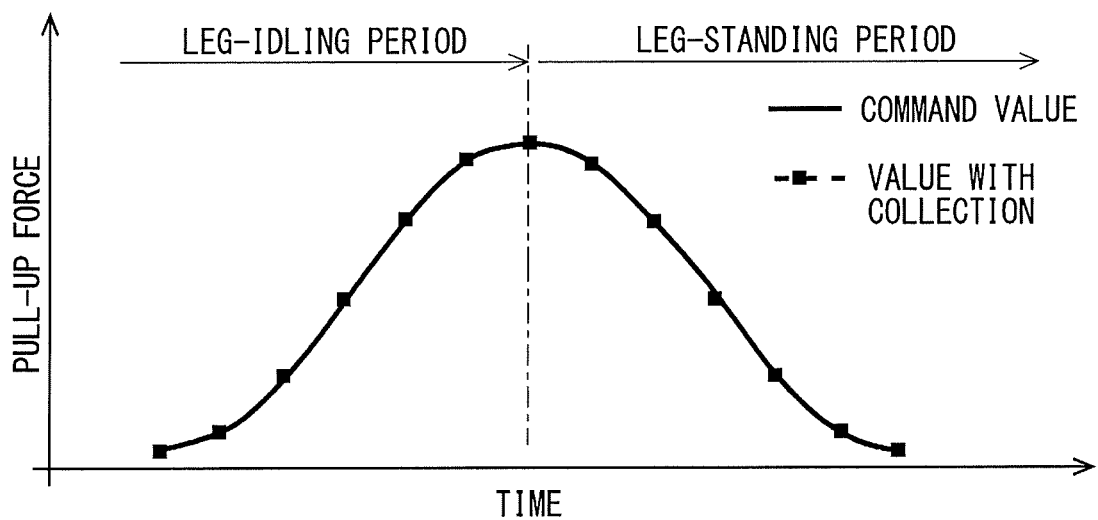
FIG. 11 is a graph showing a time change of a pull-up force with correction.

Next, an example 1 of the first embodiment is described with reference to FIGS. 9 to 11. FIG. 9 is a drawing for explaining a motion in the example 1. FIG. 10 is a graph showing a pull-up force and a command value without correction. FIG. 11 is a graph showing a pull-up force and a command value with correction. FIGS. 10 and 11 are graphs showing a time change in one walking period including leg-idling and leg-standing periods.

FIG. 9 shows a moving locus T1 of the foot A during the leg-standing period and a moving locus T2 of the foot A during the leg-idling period. Further, the moving loci T1 and T2 shown in FIG. 9 are moving loci of the foot A in the XY plane view. The foot A is grounded on a treadmill 31 (see FIGS. 1 and 3) during the leg-standing period. A moving direction of the treadmill 31 is the −X direction (rear direction). Therefore, the foot A linearly advances in the −X direction (rear direction). Accordingly, the moving locus T1 during the leg-standing period is a straight line parallel to the X direction. The displacement angle θ=0° in the leg-standing period.

On the other hand, during the leg-idling period, the foot A advances in the +X direction (front direction). In this case, in the XY plane view, it is assumed that the foot A is advancing in the +X direction in an arc-shaped manner. Therefore, the moving locus T2 has a circular arc shape during the leg-idling period. Note that the displacement amount of the foot position becomes maximum at the midpoint of the circular arc.

After releasing the foot from the ground, the displacement angle θ gradually increases as the foot goes up. Subsequently, the displacement angle θ gradually decreases as the foot goes down for grounding. Therefore, after releasing the foot from the ground, the displacement angle θ increases and then decreases. In this manner, the displacement angle θ changes with time during the leg-idling period.

Note that as shown in FIGS. 10 and 11, the command value changes according to the walking motion. The command value changes in such a manner that the pull-up force gradually increases in the leg-idling period and gradually decreases in the leg-standing period. Then, the command value of the pull-up force is maximum at the timing of changing from the leg-idling period to the leg-standing period, that is, at the timing of grounding. Further, the command value of the pull-up force is minimum at the timing of changing from the leg-standing period to the leg-idling period, that is, at the timing of releasing. The control that changes the pull-up force with time is disclosed in Japanese Unexamined Patent Application Publication No. 2017-51464, and thus the explanation thereof is omitted.

When the control device 35 does not correct the command value of the pull-up force, the pull-up force changes as shown in FIG. 10. In the leg-idling period, the displacement angle θ changes with time and the pull-up force thereby becomes less than the command value.

When the control device 35 corrects the pull-up force according to the displacement angle θ, the pull-up force becomes as shown in FIG. 11. In the leg-idling period, the command value approximately coincides with the pull-up force. Therefore, the first wire winding mechanism 33 can pull up the foot with an appropriate pull-up force. As a result, the trainee can do walking training effectively.

(Modified Example 1)

Figure 12:
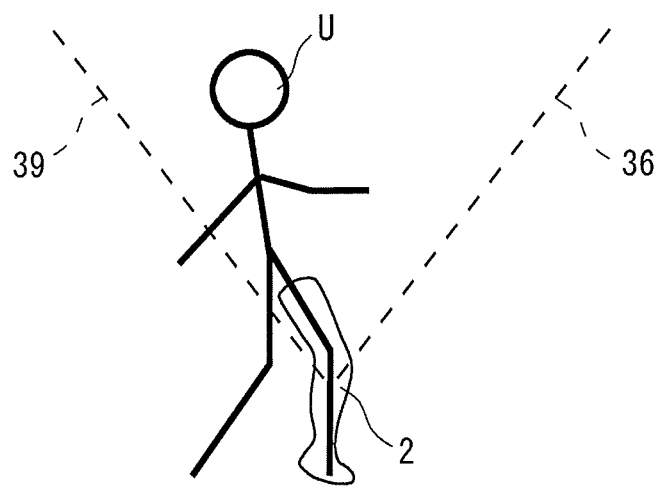
FIG. 12 is a schematic diagram for explaining the walking training apparatus according to a modified example 1.

FIG. 12 shows a modified example 1 of the first embodiment In FIG. 12, two wires 36 and 39 are attached to the walking assistance apparatus 2. The wire 36 pulls up the diseased leg from the diagonally upper direction in front of the trainee U. The wire 39 pulls up the diseased leg from the diagonally upper direction behind the trainee U. In this case, the control device 35 corrects at least one of the pull-up forces of the wires 36 and 39 according to the displacement angle θ. That is, the command value for at least one of the wires 36 and 39 is divided by cos θ to correct the same.

(Modified Example 2)

Figure 13:
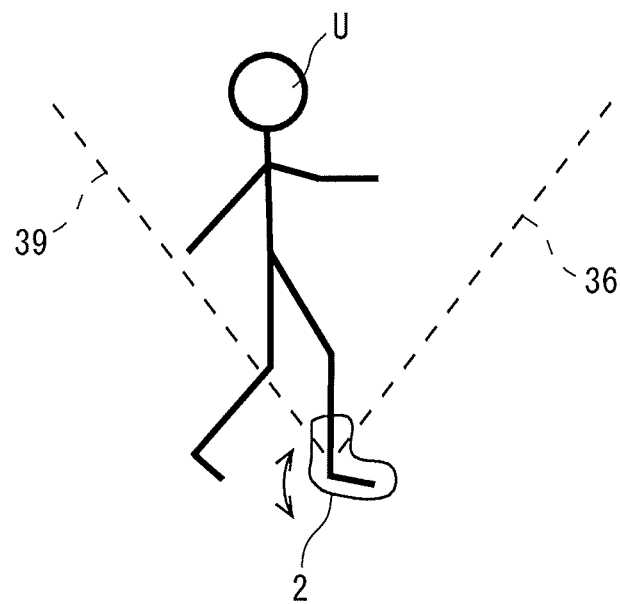
FIG. 13 is a schematic diagram for explaining the walking training apparatus according to a modified example 2.

FIG. 13 shows a modified example 2 of the first embodiment. In FIG. 13, the walking assistance apparatus 2 is a foot orthosis to be attached to the foot of the trainee. The walking assistance apparatus 2 is specifically attached to only the foot of the trainee U since it has no part for attaching to the leg of the trainee U. The walking assistance apparatus 2 assists a movement of the ankle joint. In this case, as described above, the pull-up forces of the wires 36 and 39 are corrected according to the displacement angle θ.

[Second Embodiment]

Figure 14:
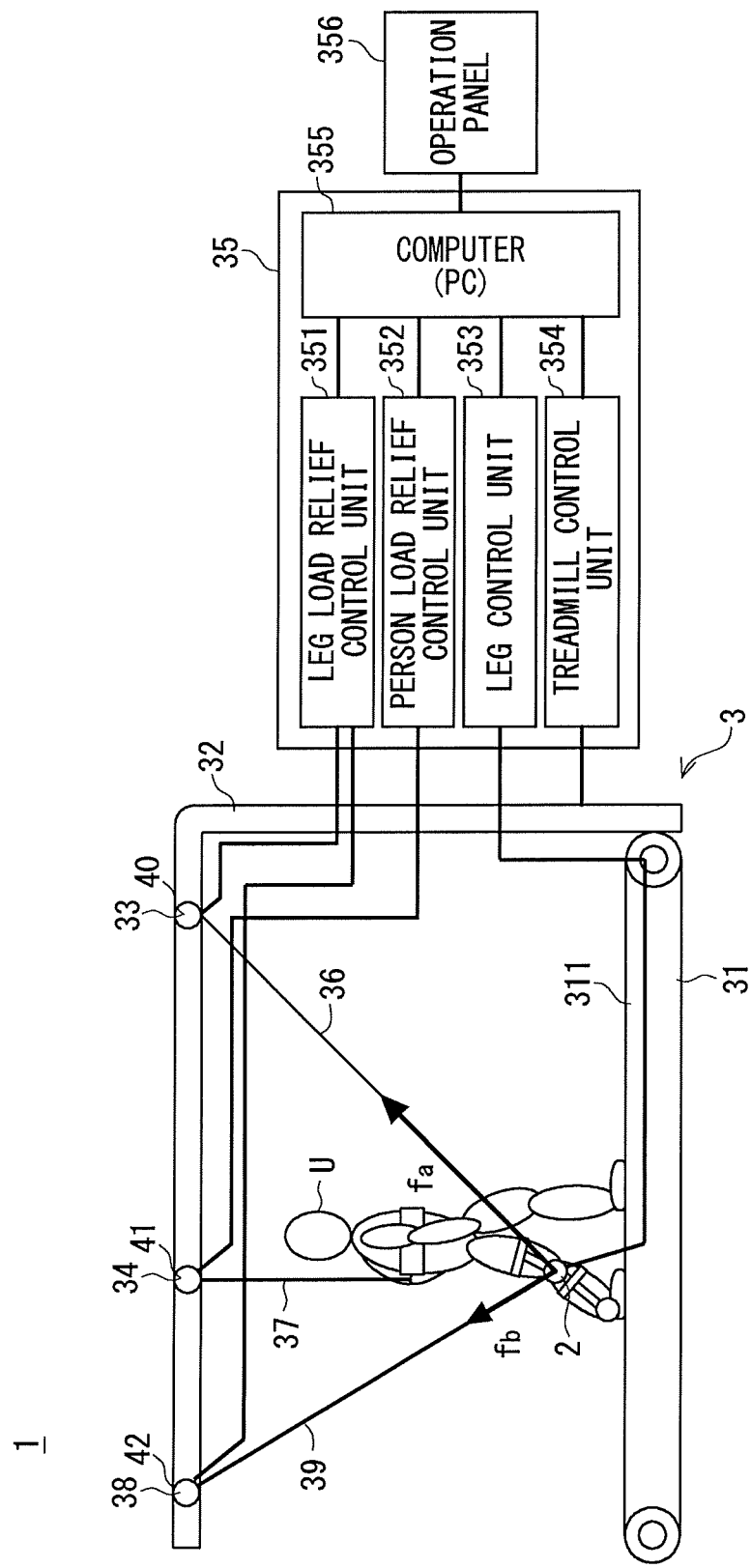
FIG. 14 is a block diagram showing a control system of the walking training apparatus according to a second embodiment.

A walking training apparatus 1 according to the second embodiment is described with reference to FIG. 14. FIG. 14 is a schematic diagram showing a control system of the walking training apparatus 1 according to the second embodiment. In the second embodiment, two wires 36 and 39 are attached to the walking assistance apparatus 2. The basic configuration except for the addition of the wire 39 is the same as that of the first embodiment and thus the explanation thereof is omitted as appropriate. For example, the person load relief control unit 352, the leg control unit 353, the treadmill control unit 354, and the like are same as those in the first embodiment.

The wire 36 pulls up the diseased leg from the diagonally upper direction in front of the trainee U. The wire 39 pulls up the diseased leg from the diagonally upper direction behind the trainee U. Therefore, a second wire winding mechanism 38 and a second storage amount detection unit 42 are added in the second embodiment.

The second wire winding mechanism 38 winds the wire 39 to apply a pull-up force for pulling up the walking assistance apparatus 2 to the wire 36. The second wire winding mechanism 38 has the same configuration as that of the first wire winding mechanism 33 and is attached to crosswise frames. The second wire winding mechanism 38 includes, for example, a mechanism for winding the wire 39 around a rotor and pulling the wire 39 from the rotor, a motor that drives this mechanism, and so on. The second wire winding mechanism 38 is positioned behind the first wire winding mechanism 33.

The second storage amount detection unit 42 detects the storage amount of the wire 39 in the second wire winding mechanism 38. Like the first storage amount detection unit 40, the second storage amount detection unit 42 includes an encoder. Further, rotation amounts of the motor and the rotor can be detected by integrating the detected value of the encoder. In this embodiment, the encoders of the first and second storage amount detection units 40 and 42 are used as sensors for detecting displacement information on connecting positions. Specifically, a connecting position can be calculated by obtaining a wire length from the storage amount detected by the first and second storage amount detection units 40 and 42. This process will be described later.

A leg load relief control unit 351 outputs the command value such that a resultant force of a vertically-upward component of the pull-up force applied by the first and second wire winding mechanisms 33 and 38 reduces the gravitational force of the walking assistance apparatus 2 to the first and second wire winding mechanisms 33 and 38. The resultant force of the vertically-upward component of the pull-up force applied by the first and second wire winding mechanisms 33 and 38 supports the weight of the walking assistance apparatus 2. Then, the resultant force of the horizontal component of the pull-up force applied by the first and second wire winding mechanisms 33 and 38 assists the start of swinging of the leg.

Figure 15:
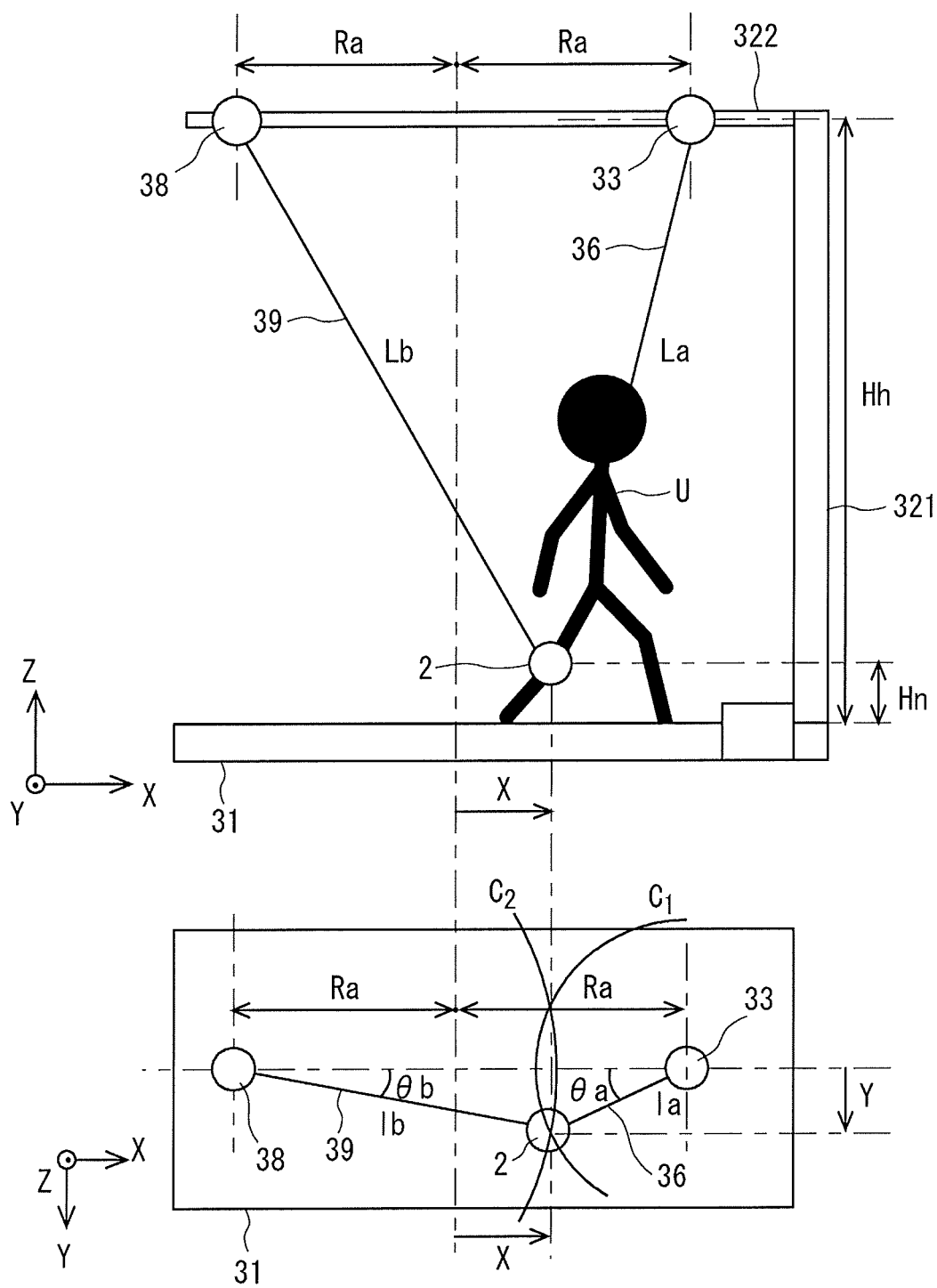
FIG. 15 is a drawing for explaining a process of obtaining a displacement angle in the walking training apparatus according to the second embodiment.

The process for detecting the connecting position from the wire length is described hereinafter with reference to FIG. 15. FIG. 15 shows a side view (XZ plane view) for explaining a process for detecting the connecting position from the wire length, and an XY plane view at the height of the knee. In FIG. 15, the walking training apparatus 1 according to the second embodiment is simplified.

As shown in FIG. 15, the wire length of the wire 36 is represented by La and the wire length of the wire 39 is represented by Lb. The attachment height of the first and second wire winding mechanisms 33 and 38 is represented by Hh. The Y positions of the first and second wire winding mechanisms 33 and 38 coincide with each other and the midpoint between the first and second wire winding mechanisms 33 and 38 is defined as an origin point. In the X direction, the distances from the origin point to the first and second wire winding mechanisms 33 and 38 are respectively represented by Ra (Ra is a positive value). That is, the X position of the first wire winding mechanism 33 is represented by +Ra and that of the second wire winding mechanism 38 is represented by −Ra. Note that Ra and Hh are constants depending on a training apparatus 3. Further, the treadmill 31 is assumed to be horizontal.

The connecting position of the wires 36 and 39 with respect to the waking assistance apparatus 2 is the knee position, and the X and Y positions at the knee position are respectively represented by X and Y. Further, the height of the knee is represented by Hn. Each wire length of the wires 36 and 39 at the knee height Hn in the XY plane are respectively represented by la and lb. Note that la and lb are expressed by the following expressions (1) and (2).

$$la = (La^2 - (Hh - Hn)^2)^{1/2} \quad (1)$$

$$lb = (Lb^2 - (Hh - Hn)^2)^{1/2} \quad (2)$$

Note that an equation of a circle C1 formed by the wire 36 having the wire length La at the knee height Hn in the XY plane is expressed by the following expression (3), and an equation of a circle C2 formed by the wire 39 having the wire length Lb at the knee height Hn in the XY plane is expressed by the following expression (4).

$$C1: (x - Ra)^2 + y^2 = la^2 \quad (3)$$

$$C2: (x + Ra)^2 + y^2 = lb^2 \quad (4)$$

Since the knee position is at the point of intersection of the circles C1 and C2, Y which is the Y position of the knee is expressed by the following expression (5).

[Expression 1]

$$Y = \pm \sqrt{lb^2 - \left(\frac{lb^2 - la^2}{4Ra} + Ra\right)^2}. \quad (5)$$

When Y is expressed using the knee height Hn and the wire lengths La and Lb, the following expression (6) is obtained.

[Expression 2]

$$Y = \pm \sqrt{Lb^2 - \left(\frac{Lb^2 - La^2}{4Ra} + Ra\right)^2 - (Hh - Hn)^2}. \quad (6)$$

Note that Ra and Hh are constants determined by the training apparatus 3. A displacement angle θa as to the wire 36 and a displacement angle θb as to the wire 39 are expressed by the following expressions (7) and (8).

$$\theta a = \sin^{-1}(Y/la) \quad (7)$$

$$\theta b = \sin^{-1}(Y/lb) \quad (8)$$

Then, when command values Fa and Fb are corrected using the displacement angles θa and θb, the following expressions (9) and (10) are obtained.

$$Fa' = Fa/\cos \theta a \qquad (9)$$

$$Fb' = Fb/\cos \theta b \qquad (10)$$

Fa' is a corrected command value given to the first wire winding mechanism 33. Fb' is a corrected command value given to the second wire winding mechanism 38. Therefore, an appropriate pull-up force can be applied to the wires 36 and 39.

As described above, the wire lengths La and Lb are obtained from the detection results of the first and second storage amount detection units 40 and 42. When the knee height Hn is determined, the knee positions (X and Y) can be calculated geometrically. Then, the command value can he corrected according to the above expressions (1) to (10). The process of obtaining the command value is executed by a computer program or the like.

Note that in the above explanation, the knee position is the connecting position of the wire. However, any positions other than the knee position may be the connecting position of the wire. Further, although the wires 36 and 39 are connected to the walking assistance apparatus 2 at the same connecting position, the connecting positions thereof may be different. Further, the Y positions of the first and second wire winding mechanisms 33 and 38 are the same, but may be different. Furthermore, the treadmill 31 may be inclined. Even in such a case, when the height of the connecting position is determined, the control device 35 can geometrically calculate the displacement angle θ from the lengths and the connecting positions of two wires. That is, the displacement angle θ can be calculated according to a geometric distance and the like depending on the configuration of the walking training apparatus 1. Therefore, the correction unit 358 can correct so that the pull-up force is appropriate.

As described in the first embodiment, the height of the connecting position may be detected by the camera 51. Alternatively, the height of the connecting position may be detected using other sensors such as the motion sensor 52, the force sensor 53, a joint angle sensor or the like.

The control device 35 may determine the height of the connecting position by the walking pattern of the trainee U. In this case, no sensor for obtaining the height of the connecting position is needed. For example, the walking pattern may be predetermined from the knee height of the trainee U standing upright. In the walking pattern, the knee height in the one walking period (the height of the connecting position) is a function of time.

For example, a pattern such that the height of the connecting position is fixed during the leg-standing period and the height of the connecting position gradually changes during the leg-idling period may he set. Obviously, the pattern such that the height of the connecting position changes during the leg-standing period may be set.

In this embodiment, the first and second storage amount detection units 40 and 42 are used as sensors for detecting the displacement angle θ. That is, the sensor for detecting the displacement angle θ is the encoder. Therefore, at least one of the encoder, the camera, the motion sensor, the force sensor and the joint angle sensor can be included as the sensor for detecting the displacement angle θ. A combination of two or more types of sensors can be used. Obviously, the sensors for detecting the displacement angle θ are not limited to the above sensors and various other types of sensors can be used.

Figure 16:
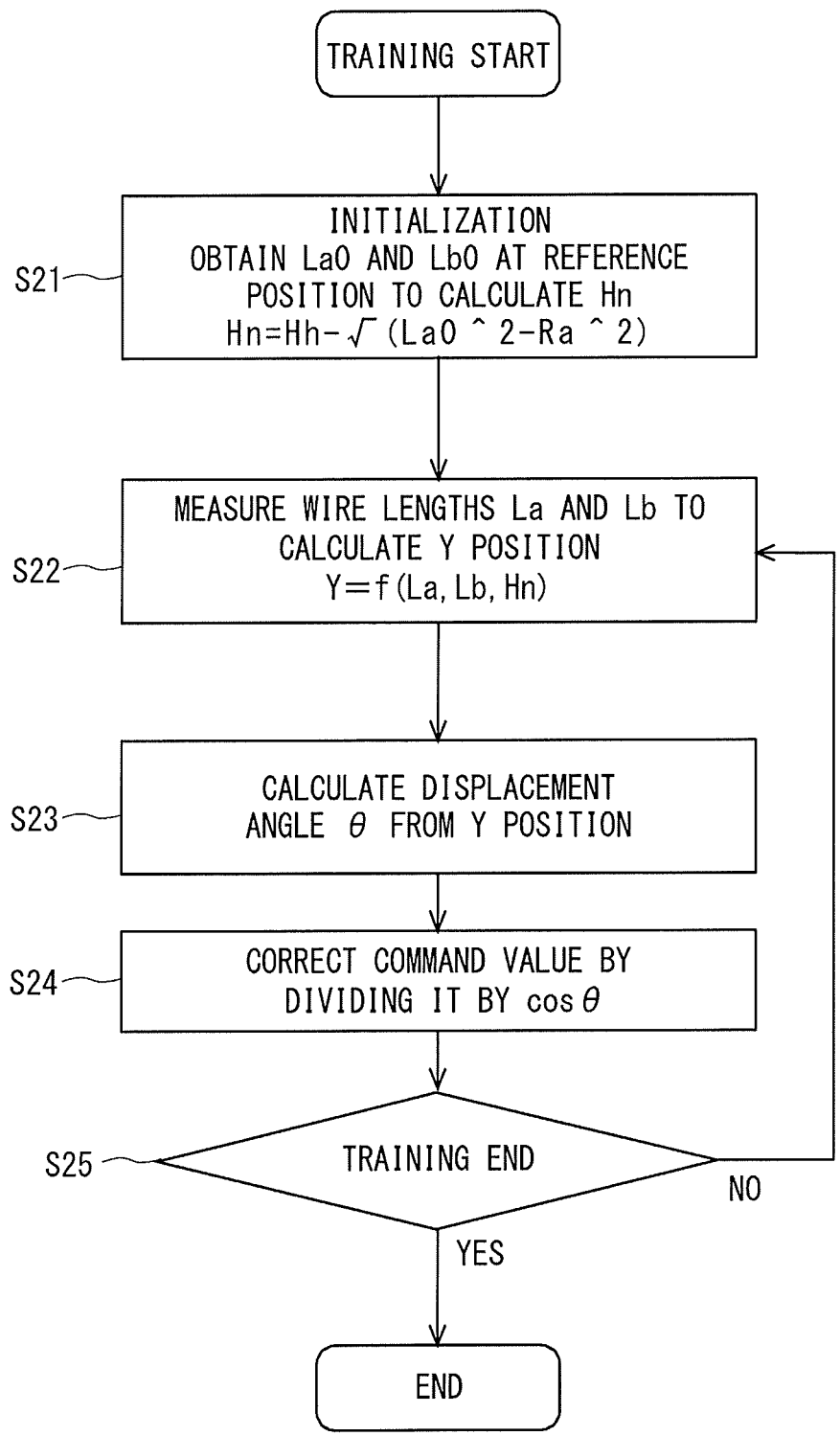
FIG. 16 is a flowchart showing a control method for the walking training apparatus according to the second embodiment.

The control method for the walking training apparatus 1 is described with reference to FIG. 16. FIG. 16 is a flowchart showing the control method. Further, this control method is explained on the assumption that the connecting positions of the wires 36 and 39 coincide with the knee position.

First, for performing the initialization, the control device 35 obtains the wire lengths La0 and Lb0 at a reference position to calculate the knee height Hn (S21). For example, the reference position is calculated in a state that the knee position is the midpoint between the first and second wire winding mechanism 33 and 38 in the XY plane and the trainee U stands upright. In the reference position, the wire lengths are obtained from the storage amounts detected by the first and second storage amount detection units 40 and 42. The knee height Hn0 at the reference position is obtained by the following expression (11).

$$Hn0 = (Hh - (La0^2 - Ra^2))^{1/2} \qquad (11)$$

Then, the walking pattern is determined by the knee height Hn0 at the reference position to obtain the knee height Hn as the function of time. Note that the knee height Hn may be obtained by the sensor such as the camera 51. In this case, the process of calculating the knee height Hn can be omitted.

The control device 35 measures the wire lengths La and Lb to obtain the Y position from the knee height Hn (S22). As shown in the expression (6), the Y position of the knee can be obtained from the wire lengths La and Lb and the knee height Hn. The knee height Hn can use a value obtained at the timing when the wire length is measured.

The control device 35 calculates the displacement angle θ from the Y position (S23). As shown in the expressions (7) and (8), the displacement angle θ can be obtained from the Y position. As shown in the expressions (9) and (10), the control device 35 divides the command value by cos θ to correct the pull-up force (S24). As a result, the corrected pull-up force is applied to the wires 36 and 39. Then, the control device 35 determines whether or not the training has finished (S25).

When it is determined that the training has not finished (NO in the S25), the process returns to S22. Thus, the control device 35 updates the Y position from the latest wire lengths La and Lb and knee height Hn. The correction is performed at the displacement angle θ according to the latest Y position. Therefore, the trainee U can do the walking training with an appropriate pull-up force. When it is determined that the training has finished (YES in the S25), the process is finished.

(Modified Example 3)

Figure 17:
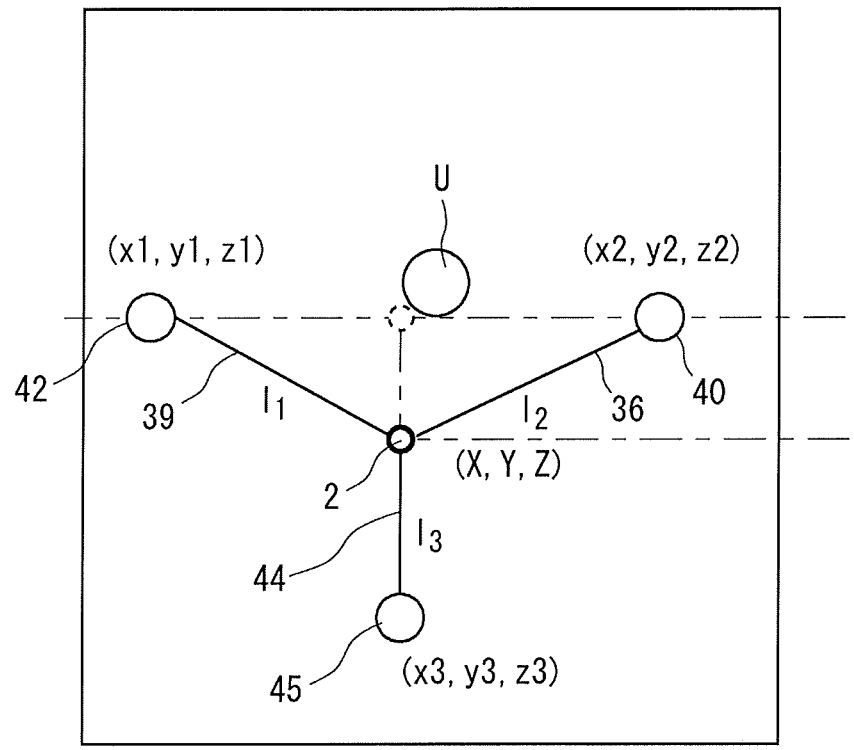
FIG. 17 is a drawing for explaining a process of obtaining a displacement angle in the walking training apparatus according to a modified example 3.

A modified example 3 of the second embodiment is described with reference to FIG. 17. FIG. 17 is a drawing for explaining a process of calculating the connecting positions (X, Y, and Z) in the modified example 3. In the modified example 3, the three wires 36, 39 and 44 are connected to the walking assistance apparatus 2. That is, the wire 44 is newly added in this example. It is assumed that the connecting positions of the three wires 36, 39 and 44 with respect to the walking assistance apparatus 2 are the same. Each of the three wires 36, 39, and 44 is connected to the walking assistance apparatus 2 from a different direction.

As shown in FIG. 17, the wire lengths of the three wires 36, 39, and 44 are represented by $l_1$, $l_2$, and $l_3$, respectively. Note that the wire 44 is wound by a fourth wire winding mechanism 45. Note that, like the other wires, the storage amount of the wire 44 stored by the fourth wire winding mechanism 45 is detected by a storage amount detection unit (not shown). Therefore, the wire lengths $l_1$, $l_2$ and $l_3$ of the three wires 36, 39 and 44 can be measured, respectively.

Then, the XYZ coordinates of the winding position of the three wires 36, 39 and 44 are (x1, y1, z1), (x2, y2, z2), and (x3, y3, z3), respectively. When it is assumed that the XYZ coordinate of the connecting position of the wire with respect to the walking assistance apparatus 2 are (X, Y, Z), the following expressions (12) to (14) hold.

$$l_1^2 = (X-x1)^2 + (Y-y1)^2 + (Z-z1)^2 \quad (12)$$

$$l_2^2 = (X-x2)^2 + (Y-y2)^2 + (Z-z2)^2 \quad (13)$$

$$l_3^2 = (X-x3)^2 + (Y-y3)^2 + (Z-z3)^2 \quad (14)$$

Therefore, the control device 35 can obtain (X, Y, Z) by the matrix calculation expressed by the following expression (15).

[Expression 3]

$$\begin{pmatrix} X \\ Y \\ Z \end{pmatrix} = \begin{pmatrix} 2(x_1 - x_2) & 2(y_1 - y_2) & 2(z_1 - z_2) \\ 2(x_2 - x_3) & 2(y_2 - y_3) & 2(z_2 - z_3) \\ 2(x_3 - x_1) & 2(y_3 - y_1) & 2(z_3 - z_1) \end{pmatrix}^{-1} \begin{pmatrix} (x_1^2 + y_1^2 + z_1^2) - (x_2^2 + y_2^2 + z_2^2) - l_1^2 + l_2^2 \\ (x_2^2 + y_2^2 + z_2^2) - (x_3^2 + y_3^2 + z_3^2) - l_2^2 + l_3^2 \\ (x_3^2 + y_3^2 + z_3^2) - (x_1^2 + y_1^2 + z_1^2) - l_3^2 + l_1^2 \end{pmatrix} \quad (15)$$

When the load relief of the leg is performed using three wires as described above, the connecting position (X, Y, Z) can be geometrically calculated by measuring the wire lengths of three wires. Therefore, there is no need to perform the process of obtaining the walking pattern in which the height of the connection position is the function of time. Further, no sensors such a camera are needed.

Note that the present disclosure is not limited to the above described embodiments and various modifications can be made without departing from the spirit of the present disclosure.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A walking training apparatus, comprising:
   an assisting orthosis configured to attach to a lower limb of a trainee;
   at least one wire connected to the lower limb directly or through the assisting orthosis;
   a drive mechanism including at least a motor and configured to wind the wire for applying a pull-up force to the wire;
   a sensor which detects displacement information according to a displacement of a position connected to the wire in a lateral direction; and
   a controller which controls the drive mechanism based on the displacement information,
   wherein a command value corresponding to the pull-up force is set for the controller,
   wherein the controller corrects the command value based on the displacement information,
   wherein the displacement information is a displacement angle θ in a wire direction from a longitudinal direction in a top view, and
   wherein the controller corrects the command value by dividing the command value by cos θ.

2. The walking training apparatus according to claim 1, wherein
   the wire comprises:
      a first wire connected to the lower limb from a diagonally upper direction in front of the trainee; and
      a second wire connected to the lower limb from a diagonally upper direction behind the trainee,
   the drive mechanism comprises:
      a first wire winding mechanism including at least a first roller and configured to wind the first wire for applying a pull-up force to the first wire; and
      a second wire winding mechanism including at least a second roller and configured to wind the second wire for applying a pull-up force to the second wire, and
   the controller corrects the command value for each of the first and second wire winding mechanisms.

3. The walking training apparatus according to claim 2, wherein
   the sensor is configured to detect a wire length of each of the first and second wires, and
   the controller calculates the displacement information based on the wire length.

4. The above walking training apparatus according to claim 1, wherein the command value before correction is changed according to a walking motion.

5. The walking training apparatus according to claim 1, wherein the sensor comprises at least one of: a camera for photographing the lower limb; a motion sensor for detecting a motion of the lower limb; a force sensor for detecting a reaction force received by the drive mechanism from the wire; or an angle sensor for detecting a joint angle of the assisting orthosis.

6. A control method for a walking training apparatus, the walking training apparatus comprising:
   an assisting orthosis configured to attach to a lower limb of a trainee;
   at least one wire connected to the lower limb directly or through the assisting orthosis;
   a drive mechanism including at least a motor and configured to wind the wire for applying a pull-up force to the wire; and
   a sensor configured to detect displacement information according to a displacement of a position connected to the wire in a lateral direction, and the control method comprising:

obtaining the displacement information based on a detection result of the sensor;

correcting the pull-up force based on the displacement information;

setting a command value corresponding to the pull-up force; and correcting the command value based on the displacement information, and wherein the displacement information is a displacement angle $\theta$ in a wire direction from a longitudinal direction in a top view, and wherein the controller corrects the command value by dividing the command value by $\cos \theta$.

* * * * *